(12) United States Patent
Omori et al.

(10) Patent No.: US 7,834,217 B2
(45) Date of Patent: Nov. 16, 2010

(54) METHOD FOR PRODUCING OXIDATION PRODUCT OF CYCLOALKANE

(75) Inventors: Takumi Omori, Himeji (JP); Yasushi Sato, Himeji (JP)

(73) Assignee: Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 12/517,287

(22) PCT Filed: Nov. 30, 2007

(86) PCT No.: PCT/JP2007/073176
§ 371 (c)(1),
(2), (4) Date: Jun. 2, 2009

(87) PCT Pub. No.: WO2008/069127
PCT Pub. Date: Jun. 12, 2008

(65) Prior Publication Data
US 2010/0081848 A1  Apr. 1, 2010

(30) Foreign Application Priority Data
Dec. 5, 2006 (JP) ............................. 2006-328794
Dec. 13, 2006 (JP) ............................. 2006-335426

(51) Int. Cl.
C07C 45/27 (2006.01)
C07C 35/08 (2006.01)
(52) U.S. Cl. .................. 568/342; 568/357; 568/836
(58) Field of Classification Search .................. 568/342
See application file for complete search history.

(56) References Cited

U.S. PATENT DOCUMENTS

| 5,859,301 | A | 1/1999 | Kragten et al. |
| 5,892,122 | A | 4/1999 | Ostermaier et al. |
| 5,905,173 | A | 5/1999 | Kragten et al. |
| 6,642,419 | B1 | 11/2003 | Miura et al. |
| 2005/0020439 | A1 | 1/2005 | Ishii et al. |

FOREIGN PATENT DOCUMENTS

| JP | 7-247230 A | 9/1995 |
| JP | 8-38909 A | 2/1996 |
| JP | 9-143109 A | 6/1997 |
| JP | 9-194408 A | 7/1997 |
| JP | 2000-239200 A | 9/2000 |
| JP | 2003-128602 A | 5/2003 |
| JP | 3426213 B2 | 7/2003 |
| JP | 2004-59515 A | 2/2004 |
| JP | 2004-59541 A | 2/2004 |
| WO | WO-03/055600 A1 | 7/2003 |

*Primary Examiner*—Sikarl A Witherspoon
(74) *Attorney, Agent, or Firm*—Birch Stewart Kolasch & Birch, LLP

(57) ABSTRACT

Disclosed is a method for industrially efficiently producing a corresponding useful oxidation product such as a cycloalkyl hydroperoxide, a cycloalkanol, and/or a cycloalkanone, especially a particularly useful cycloalkanone, from a cycloalkane with a high selectivity in a good yield at low cost. This method is advantageous in respect of energy and process. Specifically, an oxidation product of a cycloalkane is obtained by oxidizing the cycloalkane in a liquid-liquid two phase system using an aqueous solvent in the presence of a nitrogen atom-containing cyclic compound which contains, as its ring constituent, a structure represented by following Formula (I):

[Chemical Formula 1]

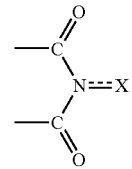

(I)

wherein X represents an oxygen atom or an —OR group, and wherein R represents a hydrogen atom or a hydroxyl-protecting group,
and which has a solubility in water at 25° C. of 0.5 g/100 g-$H_2O$ or more.

5 Claims, No Drawings

METHOD FOR PRODUCING OXIDATION PRODUCT OF CYCLOALKANE

TECHNICAL FIELD

The present invention relates to methods for producing oxidation reaction products of cycloalkanes. Of cycloalkyl hydroperoxides, cycloalkanols, and cycloalkanones as oxidation reaction products of cycloalkanes, the cycloalkyl hydroperoxides are useful as raw materials for the production of cycloalkanols and cycloalkanones; and the cycloalkanols are useful as raw materials for the production of cycloalkanones. The cycloalkanols and cycloalkanones are useful as raw materials for the production of polymeric compounds such as polyamide compounds, and as intermediate materials for the production of "fine chemicals" (specialty chemicals).

BACKGROUND ART

As a method for producing oxidation products of cycloalkanes, there has been known a method for oxidizing a cycloalkane with air by the catalysis of a transition metal compound such as a cobalt compound (see Japanese Unexamined Patent Application Publication (JP-A) No. H09-143109). This method, however, is disadvantageous in that the yield of a target oxidation product is generally low, and when the reaction is conducted for a prolonged time period in order to improve the conversion, the selectivity for the oxidation product is reduced. Additionally, the transition metal compound such as a cobalt compound, if contained in the product, may adversely affect typically a subsequent reaction or the properties of a downstream product, and this requires extra separation facilities for reliably removing such transition metal compound.

As a possible solution to these problems, there has been proposed a method for producing an oxidation product of a cycloalkane without using a cobalt compound, by oxidizing the cycloalkane in the presence of an imide compound having a cyclic imide skeleton (cyclic imide compound) (see JP-A No. 2003-128602). According to this method, an oxidation product of a cycloalkane can be produced with a high selectivity.

However, in the reaction using a cyclic imide compound as a catalyst in JP-A No. 2003-128602, the way to feed the cyclic imide compound to the reaction system is a problem, because the cyclic imide compound has a low solubility in the substrate. A major solution taken to this problem is dissolving the cyclic imide compound in an organic solvent. However, use of such an organic solvent is energetically disadvantageous, because this requires an extra operation, such as distillation, in a purification step so as to remove the organic solvent.

On the other hand, a reaction for converting a cycloalkyl hydroperoxide into a cycloalkanone and a cycloalkanol is one of industrially useful reactions and is used typically in a process of producing KA oil (a mixture of cyclohexanone and cyclohexanol) through oxidation of cyclohexane with oxygen. This reaction is generally carried out by mixing a liquid containing a cycloalkyl hydroperoxide with a transition metal catalyst, or an alkaline aqueous solution, or both, and a variety of techniques therefore have been reported.

JP-A No. H07-247230 discloses a method for producing an alkanone and/or an alkanol, by oxidizing an alkane and/or an alkene with oxygen to give an alkyl hydroperoxide and decomposing the alkyl hydroperoxide by the catalysis of a metallic compound catalyst such as a magnesium compound in the presence of a separated aqueous phase having a pH of more than 8.5, in which the catalyst is supported on a supporting material. JP-A No. H09-194408 discloses a method for producing a cycloalkanone and/or a cycloalkanol by decomposing a cycloalkyl hydroperoxide in the presence of an aqueous phase containing an alkali metal hydroxide and an alkali metal salt. JP-A No. 2004-59515 discloses a method for converting a cycloalkyl hydroperoxide into a cycloalkanone and a cycloalkanol by mixing a liquid containing the cycloalkyl hydroperoxide with a transition metal hydroxide and an alkaline (basic) aqueous solution. JP-A No. 2004-59541 discloses a method for converting a cycloalkyl hydroperoxide into a cycloalkanone and a cycloalkanol by mixing a liquid containing the cycloalkyl hydroperoxide with an N-hydroxy cyclic imide, a cobalt compound, and an alkaline aqueous solution.

Of cycloalkanones and cycloalkanols obtained by these methods, the cycloalkanols should be dehydrogenized so as to give cycloalkanones in many cases. Ultimately, high selectivity for cycloalkanones is desirable in decomposition reactions of cycloalkyl hydroperoxides. According to the above methods, however, the production ratios of cycloalkanones to cycloalkanols are low, and even when being high, at the best about 1.5. Additionally, according to the methods, cycloalkyl hydroperoxides are generally decomposed in the presence of a strong alkaline aqueous solution such as an aqueous sodium hydroxide solution so as to increase the decomposition rates of the cycloalkyl hydroperoxides. However, a strong alkaline aqueous solution such as an aqueous sodium hydroxide solution, if used in the reaction, causes undesirable oligomerization of cycloalkanones in a subsequent distillation step for separating the cycloalkanones and cycloalkanols, and to avoid this, there is a need of providing an extra neutralization step (Japanese Patent No. 3426213). This is a cause of increasing the production cost of cycloalkanones and cycloalkanols.

[Patent Document 1] JP-A No. H09-143109
[Patent Document 2] JP-A No. 2003-128602
[Patent Document 3] JP-A No. H07-247230
[Patent Document 4] JP-A No. H09-194408
[Patent Document 5] JP-A No. 2004-59515
[Patent Document 6] JP-A No. 2004-59541
[Patent Document 7] Japanese Patent No. 3426213

DISCLOSURE OF INVENTION

Problems to be Solved by the Invention

Accordingly, an object of the present invention is to provide a method for industrially efficiently producing a corresponding useful oxidation product such as a cycloalkyl hydroperoxide, a cycloalkanol, and a cycloalkanone, especially a particularly useful cycloalkanone, from a cycloalkane with a high selectivity in a good yield at low cost, which method is advantageous in respect of energy and process.

Means for Solving the Problems

The present inventors focused attention on that methods for producing an oxidation product through oxidation of a cycloalkane generally include a peroxide decomposition step, a hydrolysis step, and/or a water washing step after the completion of the oxidation reaction and before a purification step and, in this case, the methods always include a step of extracting an organic phase and an aqueous phase. Thus, they made investigations on methods using water as a solvent. As a result, they have found that, when a reaction is carried out in a liquid-liquid two phase system using water as a solvent by the catalysis of a compound being highly soluble in water and being chosen from cyclic imide compounds, not only the catalyst can be easily fed to the reaction system, but also the catalytic function of the catalyst does not deteriorate and the oxidation reaction smoothly proceeds to thereby give a target oxidation reaction product in a good yield. They have also found that, according to this technique, the catalyst can be easily separated from the reaction product after the reaction, and the technique is therefore more advantageous in respect of energy and process than methods using organic solvents and thus enables efficient production of an oxidation product of a cycloalkane. In addition, they have found that, by mixing a liquid containing a cycloalkyl hydroperoxide with a basic aqueous solution having a pH of 12 or less in the presence of the catalyst, the production ratio of cycloalkanone to cycloalkanol is remarkably improved and the target compound can be produced at low cost. The present invention has been made based on these findings and further investigations.

Specifically, the present invention provides a method for producing an oxidation product of a cycloalkane. This method includes the step of oxidizing the cycloalkane in a liquid-liquid two phase system using an aqueous solvent in the presence of a nitrogen-containing cyclic compound to give an oxidation product of the cycloalkane, in which the nitrogen-containing cyclic compound contains, as its ring constituent, a skeleton represented by following Formula (I)

[Chemical Formula 1]

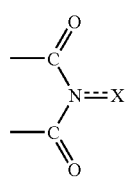

(I)

wherein X represents an oxygen atom or an —OR group, and wherein R represents a hydrogen atom or a hydroxyl-protecting group, and the nitrogen-containing cyclic compound has a solubility in water at 25° C. of 0.5 g/100 g-$H_2O$ or more.

The nitrogen-containing cyclic compound can be, for example, N-hydroxysuccinimide.

It is preferred that, after the step of oxidizing the cycloalkane, a cycloalkyl hydroperoxide contained in the oxidation product of the cycloalkane is mixed with a basic aqueous solution having a pH of 12 or less in the presence of the nitrogen-containing cyclic compound containing a skeleton of Formula (I) as its ring constituent, to thereby decompose and convert the cycloalkyl hydroperoxide into a cycloalkanone and a cycloalkanol, The basic aqueous solution is preferably an aqueous solution containing a compound selected from the group consisting of alkali metal carbonates and alkaline earth metal carbonates.

ADVANTAGES

According to the present invention, the oxidation of a cycloalkane is carried out in a liquid-liquid two phase system using an aqueous solvent by the catalysis of a nitrogen-containing cyclic compound which has a specific skeleton and which is highly soluble in water. Therefore the catalyst can be easily fed to the reaction system and sufficiently exhibits its function to allow an oxidation reaction to proceed smoothly to thereby give a target oxidation reaction product in a good yield. In addition, since the catalyst after the reaction can be easily separated from the reaction product and unreacted cycloalkane, the method is more advantageous both in respect of energy and process than methods using organic solvents and can industrially efficiently produce an oxidation product of a cycloalkane.

Further, by decomposing a cycloalkyl hydroperoxide in the oxidation product of the cycloalkane into a cycloalkanone and a cycloalkanol, the production ratio of cycloalkanone to cycloalkanol in the oxidation product of the cycloalkane can be remarkably improved. This significantly reduces the load in the step of producing a cycloalkanone through a dehydrogenation reaction of a cycloalkanol. Additionally, there is no need of using a strong alkali (strongly basic substance), and the oligomerization of a cycloalkanone in a distillation step can be prevented. The method is therefore more advantageous in respect both of energy and process than the known methods and can industrially efficiently produce oxidation products, mainly containing a cycloalkanone, of a cycloalkane at low cost.

BEST MODES FOR CARRYING OUT THE INVENTION

[Cycloalkane]

In the present invention, a cycloalkane (hereinafter also simply referred to as "substrate") is used as a starting compound.

Exemplary cycloalkanes include cycloalkanes having about 3 to about 30 members, such as cyclopropane, cyclobutane, cyclopentane, cyclohexane, cycloheptane, cyclooctane, cyclononane, cyclodecane, cyclododecane, cyclotetradecane, cyclohexadecane, cyclooctadecane, cycloicosane, cyclodocosane, and cyclotriacontane. Among them, preferred are cycloalkanes having about 4 to about 20 members, such as cyclopentane, cyclohexane, cyclooctane, and cyclododecane, of which those having about 5 to about 16 members are more preferred.

The cycloalkane may have one or more substituents within ranges not adversely affecting the reaction. Examples of such substituents include halogen atoms, oxo group, hydroxyl group, mercapto group, substituted oxy groups (e.g., alkoxy groups, aryloxy groups, and acyloxy groups), substituted thio groups, carboxyl group, substituted oxycarbonyl groups, substituted or unsubstituted carbamoyl groups, cyano group, nitro group, substituted or unsubstituted amino groups, alkyl groups (e.g., alkyl groups having 1 to 20 carbon atoms, such as methyl, ethyl, isopropyl, t-butyl, hexyl, octyl, and decyl groups, of which alkyl groups having 1 to 4 carbon atoms are preferred), alkenyl groups, alkynyl groups, cycloalkyl groups, cycloalkenyl groups, aryl groups (e.g., phenyl and naphthyl groups), aralkyl groups (e.g., benzyl group), and heterocyclic groups.

[Oxidizing Agent]

Oxygen can be used as an oxidizing agent herein. The oxygen is preferably molecular oxygen. The molecular oxygen is not especially limited and can be any of pure oxygen; a diluted oxygen diluted with an inert gas such as nitrogen, helium, argon, or carbon dioxide gas; and air. When a diluted oxygen (oxygen-containing gas; such as a gaseous mixture of oxygen and nitrogen) is used, the oxygen concentration in the oxygen-containing gas is, for example, from about 3 to about 95 percent by volume, and preferably from about 5 to about 83 percent by volume. The oxygen may be generated within the reaction system. Though varying depending on the type of the substrate, the amount of oxygen is generally about 0.5 mole or more (e.g., about 1 mole or more), preferably from about 1 to about 100 moles, and more preferably from about 2 to about 50 moles, per 1 mole of the substrate. Oxygen is used in excess to the substrate in many cases.

[Catalyst]

The compound used herein as the catalyst is a nitrogen-containing cyclic compound containing a skeleton represented by Formula (I) as its ring constituent and having a solubility in water at 25° C. of 0.5 g/100 g-H₂O or more. A compound of this type, if used as the catalyst, can be fed in the form of a solution dissolved in water (aqueous solution) to the reaction system, thereby not only excels in operability and workability, but also effectively functions as the catalyst in an oxidation reaction of a cycloalkane in a liquid-liquid two phase system using an aqueous solvent to allow the oxidation reaction to proceed smoothly to thereby give a target oxidation product in a good yield. In contrast, when a nitrogen-containing cyclic compound having a skeleton represented by Formula (I) as its ring constituent but having a solubility in water at 25° C. of less than 0.5 g/100 g-H₂O is used as a catalyst, the catalyst is sparingly soluble both in the substrate and in water, the reaction system becomes a heterogenous system, the catalyst does not sufficiently exhibit its function, and this renders it difficult to obtain a target oxidation reaction product in a good yield.

In Formula (I), the bond between nitrogen atom and X is a single bond or double bond. The nitrogen-containing cyclic compound may have two or more skeletons represented by Formula (I) per molecule. In the nitrogen-containing cyclic compound wherein X is an —OR group and R is a hydroxyl-protecting group, two or more of the moiety, other than R, of the skeleton represented by Formula (I) wherein X is an —OR group may be bonded with each other through R.

In Formula (I), the hydroxyl-protecting group represented by R can be any hydroxyl-protecting group commonly used in the field of organic synthesis. Examples of such protecting groups include alkyl groups (e.g., alkyl groups having 1 to 4 carbon atoms, such as methyl and t-butyl groups), alkenyl groups (e.g., allyl group), cycloalkyl groups (e.g., cyclohexyl group), aryl groups (e.g., 2,4-dinitrophenyl group), aralkyl groups (e.g., benzyl, 2,6-dichlorobenzyl, 3-bromobenzyl, 2-nitrobenzyl, and triphenylmethyl groups); groups that can form an acetal or hemiacetal group with a hydroxyl group, including substituted methyl groups (e.g., methoxymethyl, methylthiomethyl, benzyloxymethyl, t-butoxymethyl, 2-methoxyethoxymethyl, 2,2,2-trichloroethoxymethyl, bis(2-chloroethoxy)methyl, and 2-(trimethylsilyl)ethoxymethyl groups), substituted ethyl groups (e.g., 1-ethoxyethyl, 1-methyl-1-methoxyethyl, 1-isopropoxyethyl, 2,2,2-trichloroethyl, and 2-methoxyethyl groups), tetrahydropyranyl group, tetrahydrofuranyl group, and 1-hydroxyalkyl groups (e.g., 1-hydroxyethyl, 1-hydroxyhexyl, 1-hydroxydecyl, 1-hydroxyhexadecyl, and 1-hydroxy-1-phenylmethyl groups); acyl groups (e.g., aliphatic saturated or unsaturated acyl groups including aliphatic acyl groups having 1 to 20 carbon atoms, such as formyl, acetyl, propionyl, butyryl, isobutyryl, valeryl, pivaloyl, hexanoyl, heptanoyl, octanoyl, nonanoyl, decanoyl, lauroyl, myristoyl, palmitoyl, and stearoyl groups; acetoacetyl group; alicyclic acyl groups including cycloalkanecarbonyl groups such as cyclopentanecarbonyl and cyclohexanecarbonyl groups; and aromatic acyl groups such as benzoyl and naphthoyl groups), sulfonyl groups (e.g., methanesulfonyl, ethanesulfonyl, trifluoromethanesulfonyl, benzenesulfonyl, p-toluenesulfonyl, and naphthalenesulfonyl groups), alkoxycarbonyl groups (e.g., alkoxy-carbonyl groups whose alkoxy moiety having 1 to 4 carbon atoms, such as methoxycarbonyl, ethoxycarbonyl, and t-butoxycarbonyl groups), aralkyloxycarbonyl groups (e.g., benzyloxycarbonyl group and p-methoxybenzyloxycarbonyl group), substituted or unsubstituted carbamoyl groups (e.g., carbamoyl, methylcarbamoyl and phenylcarbamoyl groups), groups corresponding to inorganic acids (e.g., sulfuric acid, nitric acid, phosphoric acid, and boric acid), except for removing OH group therefrom, dialkylphosphinothioyl groups (e.g., dimethylphosphinothioyl group), diarylphosphinothioyl groups (e.g., diphenylphosphinothioyl group), and substituted silyl groups (e.g., trimethylsilyl, t-butyldimethylsilyl, tribenzylsilyl, and triphenylsilyl groups).

When X is an —OR group and two or more of the other moiety of the skeleton represented by Formula (I) than R are bonded to each other through R, examples of the group R include acyl groups corresponding to polycarboxylic acids, such as oxalyl, malonyl, succinyl, glutaryl, phthaloyl, isophthaloyl, and terephthaloyl groups; carbonyl group; and multivalent hydrocarbon groups such as methylene, ethylidene, isopropylidene, cyclopentylidene, cyclohexylidene, and benzylidene groups, of which groups that can form acetal bonds with two hydroxyl groups are preferred.

Preferred examples of R include hydrolyzable protecting groups that can be removed through hydrolysis such as hydrogen atom; groups that can form an acetal or hemiacetal group with a hydroxyl group; groups corresponding to acids such as carboxylic acids, sulfonic acids, carbonic acids, carbamic acids, sulfuric acid, phosphoric acid, and boric acid, except for removing OH group therefrom (e.g., acyl groups, sulfonyl groups, alkoxycarbonyl groups, and carbamoyl groups), and the other hydrolyzable protecting groups that can be removed through hydrolysis. Among them, hydrogen atom is especially preferred as R.

Exemplary nitrogen-containing cyclic compounds each containing a skeleton represented by Formula (I) as a ring constituent include cyclic imide compounds each having a cyclic imide skeleton represented by following Formula (I):

[Chemical Formula 2]

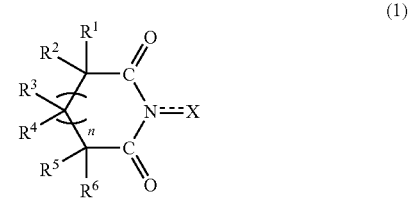

(1)

wherein "n" denotes 0 or 1; X represents an oxygen atom or an —OR group, wherein R represents a hydrogen atom or a hydroxyl-protecting group; and R¹, R², R³, R⁴, R⁵, and R⁶ are the same as or different from one another and each represent a hydrogen atom, a halogen atom, an alkyl group, an aryl group, a cycloalkyl group, a hydroxyl group, an alkoxy group, a carboxyl group, a substituted oxycarbonyl group, an acyl group, or an acyloxy group, where at least two of R¹, R², R³, R⁴, R⁵, and R⁶ may be combined to form a double bond, an aromatic ring, or a nonaromatic ring together with a carbon atom or carbon-carbon bond constituting the cyclic imide skeleton, and wherein one or more cyclic imido groups represented by following Formula (a):

[Chemical Formula 3]

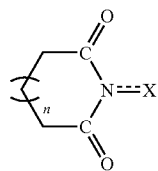

(a)

wherein "n" and X are as defined above may be further formed in the substituents $R^1$, $R^2$, $R^3$, $R^4$, $R^5$, and/or $R^6$ or on the double bond or aromatic or nonaromatic ring formed by at least two of $R^1$, $R^2$, $R^3$, $R^4$, $R^5$, and $R^6$.

Of the substituents $R^1$, $R^2$, $R^3$, $R^4$, $R^5$, $R^6$ in cyclic imide compounds represented by Formula (1), exemplary halogen atoms include iodine, bromine, chlorine, and fluorine atoms. Exemplary alkyl groups include linear or branched alkyl groups having about 1 to about 4 carbon atoms, such as methyl, ethyl, propyl, isopropyl, and butyl groups, of which those having about 1 or 2 carbon atoms are preferred.

Exemplary aryl groups include phenyl and tolyl groups; and exemplary cycloalkyl groups include cyclopentyl and cyclohexyl groups. Exemplary alkoxy groups include alkoxy groups having about 1 to about 4 carbon atoms, such as methoxy, ethoxy, isopropoxy, butoxy, and t-butoxy groups, of which those having about 1 or 2 carbon atoms are preferred.

Exemplary substituted oxycarbonyl groups include alkoxy-carbonyl groups whose alkoxy moiety having 1 to 4 carbon atoms, such as methoxycarbonyl, ethoxycarbonyl, isopropoxycarbonyl, butoxycarbonyl, and t-butoxycarbonyl groups, of which alkoxy-carbonyl groups whose alkoxy moiety having 1 or 2 carbon atoms are preferred; cycloalkyloxy-carbonyl groups such as cyclopentyloxycarbonyl and cyclohexyloxycarbonyl groups; aryloxycarbonyl groups such as phenyloxycarbonyl group; and aralkyloxycarbonyl groups such as benzyloxycarbonyl group.

Exemplary acyl groups include aliphatic saturated or unsaturated acyl groups including aliphatic acyl groups having 1 to 5 carbon atoms, such as formyl, acetyl, propionyl, butyryl, isobutyryl, and valeryl groups, of which aliphatic acyl groups having 1 or 2 carbon atoms are preferred; acetoacetyl group; alicyclic acyl groups including cycloalkanecarbonyl groups such as cyclopentanecarbonyl and cyclohexanecarbonyl groups; and aromatic acyl groups such as benzoyl group.

Exemplary acyloxy groups include aliphatic saturated or unsaturated acyloxy groups including aliphatic acyloxy groups having 1 to 5 carbon atoms, such as formyloxy, acetyloxy, propionyloxy, butyryloxy, isobutyryloxy, and valeryloxy groups, of which aliphatic acyloxy groups having 1 or 2 carbon atoms are preferred; acetoacetyloxy group; alicyclic acyloxy groups including cycloalkanecarbonyloxy groups such as cyclopentanecarbonyloxy and cyclohexanecarbonyloxy groups; and aromatic acyloxy groups such as benzoyloxy group.

The substituents $R^1$, $R^2$, $R^3$, $R^4$, $R^5$, and $R^6$ are the same as or different from one another. At least two of $R^1$, $R^2$, $R^3$, $R^4$, $R^5$, and $R^6$ in Formula (1) may be combined to form a double bond, an aromatic ring, or a nonaromatic ring together with a carbon atom or carbon-carbon bond constituting the cyclic imide skeleton. The aromatic or nonaromatic ring is preferably a ring having about 5 to about 12 members, and more preferably a ring having about 6 to about 10 members. It may be a heterocyclic or fused heterocyclic ring but is often a hydrocarbon ring. The ring may have one or more substituents such as alkyl groups, haloalkyl groups, hydroxyl group, alkoxy groups, carboxyl group, substituted oxycarbonyl groups, acyl groups, acyloxy groups, nitro group, cyano group, amino group, and halogen atoms.

One or more cyclic imido groups represented by Formula (a) may further be formed on the substituents $R^1$, $R^2$, $R^3$, $R^4$, $R^5$, and/or $R^6$ and/or on the double bond or aromatic or non-aromatic ring formed by at least two of $R^1$, $R^2$, $R^3$, $R^4$, $R^5$, and $R^6$. Typically, when $R^1$, $R^2$, $R^3$, $R^4$, $R^5$ or $R^6$ is an alkyl group having 2 or more carbon atoms, the cyclic imido group may be formed as including adjacent two carbon atoms constituting the alkyl group. When at least two of $R^1$, $R^2$, $R^3$, $R^4$, $R^5$, and $R^6$ are combined to form a double bond together with a carbon-carbon bond constituting the cyclic imide skeleton, the cyclic imido group may be formed as including the double bond. When at least two of $R^1$, $R^2$, $R^3$, $R^4$, $R^5$, and $R^6$ are combined to form an aromatic or nonaromatic ring together with a carbon atom or carbon-carbon bond constituting the cyclic imide skeleton, the cyclic imido group may be formed as including adjacent two carbon atoms constituting the ring.

Preferred exemplary cyclic imide compounds include compounds represented by following formulae:

[Chemical Formula 4]

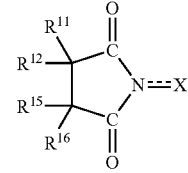

(1a)

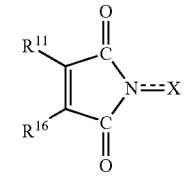

(1b)

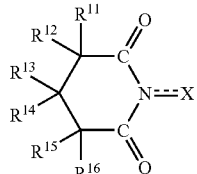

(1c)

wherein $R^{11}$ to $R^{16}$ are the same as or different from one another and each represent a hydrogen atom, a halogen atom, an alkyl group, an aryl group, a cycloalkyl group, a hydroxyl group, an alkoxy group, a carboxyl group, a substituted oxycarbonyl group, an acyl group, or an acyloxy group; and X is as defined above.

Examples of the halogen atoms, alkyl groups, aryl groups, cycloalkyl groups, hydroxyl group, alkoxy groups, carboxyl group, substituted oxycarbonyl groups, acyl groups, and acyloxy groups as the substituents $R^{11}$ to $R^{16}$ include the same groups listed as the corresponding groups on $R^1$ to $R^6$.

Of preferred cyclic imide compounds, representative examples of compounds having a 5-membered cyclic imide skeleton include compounds of Formula (1) in which X is an —OR group and R is a hydrogen atom, such as N-hydroxysuccinimide, N-hydroxy-α-methylsuccinimide, N-hydroxy-α,α-dimethylsuccinimide, N-hydroxy-α,β-dimethylsuccinimide, N-hydroxymaleimide, and α,β-diacetoxy-N-hydroxysuccinimide.

Of preferred cyclic imide compounds, representative examples of compounds having a 6-membered cyclic imide skeleton include compounds of Formula (1) in which X is an —OR group and R is a hydrogen atom, such as N-hydroxyglutarimide, N-hydroxy-α,α-dimethylglutarimide, and N-hydroxy-β,β-dimethylglutarimide.

Exemplary nitrogen-containing cyclic compounds containing a skeleton represented by Formula (I) as a ring constituent further include, in addition to the cyclic imide compounds, cyclic acylurea compounds having a cyclic acylurea skeleton [—C(=O)—N—C(=O)—N–]. Representative examples of such cyclic acylurea compounds include hydro-1-hydroxy (or 1-substituted oxy)-1,3,5-triazine-2,6-dione compounds represented by following Formula (2):

[Chemical Formula 5]

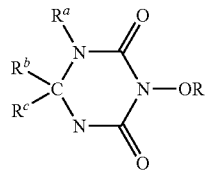

(2)

wherein $R^a$ and $R^d$ are the same as or different from each other and each represent a hydrogen atom, an alkyl group, an aryl group, a cycloalkyl group, an unprotected or protected hydroxyl group, an unprotected or protected carboxyl group, or an acyl group; $R^b$ and $R^c$ are the same as or different from each other and each represent a hydrogen atom, a halogen atom, an alkyl group, an aryl group, a cycloalkyl group, a hydroxyl group, an alkoxy group, a carboxyl group, a substituted oxycarbonyl group, an acyl group, or an acyloxy group, wherein at least two of $R^a$, $R^b$, $R^c$, and $R^d$ may be combined to form a double bond, an aromatic ring, or a nonaromatic ring together with an atom constituting the ring in the formula, and wherein $R^b$ and $R^c$ may together form an oxo group; and R is as defined above.

Exemplary alkyl groups, aryl groups, cycloalkyl groups, and acyl groups as $R^a$ and $R^d$ in Formula (2) include the same groups such as the alkyl groups and other corresponding groups exemplified in $R^1$ to $R^6$. Exemplary hydroxyl-protecting groups are as above.

Exemplary carboxyl-protecting groups include protecting groups commonly used in the field of organic synthesis, including alkoxy groups (e.g., alkoxy groups having 1 to 6 carbon atoms, such as methoxy, ethoxy, and butoxy), cycloalkyloxy groups, acyloxy groups (e.g., phenoxy group), aralkyloxy groups (e.g., benzyloxy group), trialkylsilyloxy groups (e.g., trimethylsilyloxy group), unsubstituted or substituted amino groups (e.g., amino group; and mono- or di-($C_1$-$C_6$ alkyl)amino groups such as methylamino group and dimethylamino group.

Exemplary halogen atoms, alkyl groups, aryl groups, cycloalkyl groups, hydroxyl groups, alkoxy groups, carboxyl groups, substituted oxycarbonyl groups, acyl groups, and acyloxy groups as $R^b$ and $R^c$ include the same groups such as the alkyl groups and other corresponding groups exemplified as $R^1$ to $R^6$.

In Formula (2), at least two of $R^a$, $R^b$, $R^c$, and $R^d$ may be combined to form a double bond, an aromatic ring, or a nonaromatic ring together with an atom (carbon atom and/or nitrogen atom) constituting the ring in the formula, and $R^b$ and $R^c$ may together form an oxo group. Preferred examples of the aromatic or nonaromatic ring are as mentioned above.

Of compounds represented by Formula (2), preferred are isocyanuric acid derivatives represented by following Formula (2a):

[Chemical Formula 6]

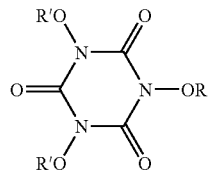

(2a)

wherein R, R', and R" are the same as or different from each other and each represent a hydrogen atom or a hydroxyl-protecting group.

Representative exemplary compounds belonging to the cyclic acylurea compounds include hexahydro-1,3,5-trihydroxy-1,3,5-triazine-2,4,6-trione (i.e., 1,3,5-trihydroxyisocyanuric acid), hexahydro-1-hydroxy-1,3,5-triazine-2,6-dione, and hexahydro-1-hydroxy-3,5-dimethyl-1,3,5-triazine-2,6-dione.

Of the nitrogen-containing cyclic compounds, a compound in which X is an —OR group and R is a hydrogen atom (N-hydroxy cyclic compound) can be produced according to a known process or a combination of such known processes. Of the nitrogen-containing cyclic compounds, a compound where X is an —OR group and R is a hydroxyl-protecting group can be produced by introducing a desired protecting group into a corresponding compound where R is a hydrogen atom (N-hydroxy cyclic compound) using a common reaction for introducing the protecting group.

Specifically, of the cyclic imide compounds, a compound where X is an —OR group and R is a hydrogen atom (N-hydroxy cyclic imide compound) can be obtained by a common imidization reaction. For example, the compound can be obtained by a process in which a corresponding acid anhydride is allowed to react with hydroxylamine for ring-opening of an acid anhydride group, and the ring is then closed to form an imide. Typically, N-acetoxysuccinimide can be obtained by allowing N-hydroxysuccinimide to react with acetic anhydride or to react with an acetyl halide in the presence of a base. As a matter of course, the compound can be produced also by any other process.

Exemplary cyclic imide compounds especially preferred as the catalyst include N-hydroxy imide compounds (e.g., N-hydroxysuccinimide) derived from aliphatic polycarboxylic acid anhydrides (cyclic anhydrides) or aromatic polycarboxylic acid anhydrides (cyclic anhydrides); and compounds obtained by introducing a protecting group into a hydroxyl group of the N-hydroxy imide compounds.

Each of different nitrogen-containing cyclic compounds each containing the skeleton represented by Formula (I) as a ring constituent may be used alone or in combination in the reaction. The catalyst containing such a nitrogen-containing cyclic compound having a skeleton represented by Formula (I) as its ring constituent may be formed within the reaction system, According to the present invention, a nitrogen-containing cyclic compound containing a skeleton represented by Formula (I) as its ring constituent and having a solubility in water at 25° C. of 0.5 g/100 g-$H_2O$ or more is used as a catalyst, as described above. The solubility in water (25° C.) is preferably 1.0 g/100 g-$H_2O$ or more, more preferably 3.0 g/100 g-$H_2O$ or more, and especially preferably 4.0 g/100 g-$H_2O$ or more. Though not especially limited, the upper limit of the solubility in water of the catalyst for use in the present invention is, for example, 100 g/100 g-$H_2O$. The catalyst for use in the present invention is especially preferably N-hydroxysuccinimide, from the points of solubility in water and catalytic activity.

The amount of the catalyst can be selected within a wide range of, for example, from about 0.000001 to about 1 mole per 1 mole of the substrate (from about 0.0001 to about 100 percent by mole). However, a high yield can be obtained according to the present invention even when the catalyst is used in a small amount, and also in view of economical efficiency and after-treatment, the amount of the imide compound per 1 mole of the substrate is preferably from about 0.000001 to about 0.01 mole (from about 0.0001 to about 1 percent by mole), and more preferably from about 0.00001 to about 0.005 mole (from about 0.001 to about 0.5 percent by mole).

The concentration of the catalyst in the reaction system is, for example, from about 0.005 to about 5 percent by weight, and preferably from about 0.02 to about 0.6 percent by weight, based on the total amount of the reaction mixture. The amount of the catalyst is, for example, from about 0.5 to about 50 percent by weight, and preferably from about 1 to about 20 percent by weight, relative to the amount of water in the reaction system.

Though a reaction in the present invention may be carried out in the presence of a transition metal compound such as a cobalt compound, the concentration of such transition metal compound in the reaction system is preferably low, because the presence of the transition metal compound may facilitate a decomposition reaction of the reaction product and may adversely affect in some uses, and this may require an extra step of removing the transition metal. Typically, the amount of a cobalt compound in terms of metal is preferably 0.0001 ppm by weight or less, and especially preferably 0.00001 ppm by weight or less. Likewise, the concentration of a compound of another transition metal in terms of metal is preferably 0.0001 ppm by weight or less, and especially preferably 0.00001 ppm by weight or less, respectively. Exemplary transition metal compounds include compounds (including elementary substances) of elements of Groups 3 to 12 of the Periodic Table of Elements, such as V, Mo, Mn, Fe, Ru, Co, and Cu.

[Reaction]

According to the present invention, an oxidation reaction of a cycloalkane is carried out in a liquid-liquid two phase system using an aqueous solvent. When the reaction is carried out in a liquid-liquid two phase system using an aqueous solvent, the catalyst can be fed, to the reaction system, in the form of a solution in water, whereby the reaction can be conducted with excellent operability and workability. Additionally, as the catalyst is being dissolved in a solvent in the reaction system, it can sufficiently exhibit its catalytic function to thereby allow the reaction to proceed smoothly. After the completion of the reaction, the reaction mixture is separated into an aqueous layer and an organic layer containing an oxidation product and unreacted cycloalkane. In this stage, the catalyst is distributed into the aqueous layer, and the catalyst can thereby be easily separated from the oxidation product and unreacted cycloalkane. In contrast, when no aqueous solvent is used, the catalyst should be fed to the reaction system in the form of a solid or a solution in an organic solvent. When the catalyst is fed in the form of a solid, the nitrogen-containing cyclic compound having a skeleton represented by Formula (I) is generally sparingly soluble in a cycloalkane, the reaction system thereby becomes heterogenous, the catalyst fails to exhibit its catalytic activity sufficiently, the conversion of cycloalkane markedly decreases, and the yield of the target compound also decreases. When the catalyst is fed to the reaction system in the form of a solution in an organic solvent, the recovery of the organic solvent by distillation after use requires much energy. In this connection, acetic acid is not preferred as the solvent, because it facilitates the formation of by-products in which the cycloalkane ring is cleaved.

The aqueous solvent for use herein can be water alone or, where necessary, a solvent mixture of water and a small amount of water-miscible organic solvent. The water-miscible organic solvent can be any solvent that is miscible with (soluble in) water and does not adversely affect the reaction, and examples thereof include acetonitrile.

The amount of the aqueous solvent is, in terms of the amount of water, for example, from 0.5 to 20 parts by weight, preferably from 0.5 to 10 parts by weight, and more preferably from 0.5 to 8 parts by weight per 100 parts by weight of the raw material cycloalkane. If the amount of water is excessively large, the concentration of catalyst decreases, and this may often cause an insufficient reaction rate. It is enough for the amount of water to be such an amount that is necessary and sufficient for dissolving a necessary amount of the catalyst.

The reaction system in the present invention may further contain additives so as to improve the rate and/or selectivity of the reaction. Exemplary additives include protic organic compounds including organic acids (e.g., carboxylic acids such as valeric acid, as well as sulfonic acids) and alcohols; and nitriles such as benzonitrile. The amount of such additives, if contained, is, for example, from about 0.0001 to about 1 mole, and preferably from about 0.001 to about 0.1 mole, per 1 mole of the substrate cycloalkane. Inorganic acids such as nitric acid may also be used as additives.

The reaction temperature is generally about 80° C. or higher (e.g., from about 80° C. to about 180° C.), preferably from about 130° C. to about 170° C., and more preferably from about 135° C. to about 155° C. If the reaction is carried out at an excessively low temperature, the reaction rate may decrease. If it is carried out at an excessively high temperature, oxidative cleavage products such as dicarboxylic acids may be produced as by-products, and this may often reduce the selectivity for a target compound (a cycloalkyl hydroperoxide, a cycloalkanol, and/or a cycloalkanone; cyclic oxidation product).

The reaction may be carried out at any pressure, i.e., under reduced pressure, at normal atmospheric pressure, or under a pressure (under a load). When the reaction is conducted under a pressure, the reaction pressure is, for example, from about 0.1 to about 20 MPa, and preferably from about 1 to about 6 MPa. Though varying depending typically on the amount of the catalyst, the oxygen partial pressure is generally from about 0.1 to about 20 MPa, and preferably from about 1 to about 5 MPa. Though varying depending on other reaction conditions, the reaction time is, for example, from about 20 minutes to about 5 hours, and preferably about 45 minutes to about 2 hours. The reaction time herein is a residence time of the reaction mixture in the case of a continuous system.

The reaction can be carried out in the presence of or under the circulation of oxygen according to a common system such as a batch system, semi-batch system, or continuous system. When the reaction is carried out according to a batch system or semi-batch system, the initial concentration of the cycloalkane may be set at preferably 80 percent by weight or more, more preferably about 90 percent by weight or more, and especially preferably 95 percent by weight or more, for better results. When the reaction is carried out according to a continuous system, the total concentration of the cycloalkane and an oxidation product thereof in a stationary state is set at preferably 80 percent by weight or more, more preferably about 90 percent by weight or more, and especially preferably 95 percent by weight or more, to give a target compound in a good yield.

After the completion of the reaction, a reaction product can be separated and purified through a separation procedure such as filtration, concentration, distillation, extraction, crystallization, recrystallization, adsorption, or column chromatography, or any combination of these procedures.

According to the present invention, a carbon atom constituting the cycloalkane ring of the cycloalkane used as the raw material is oxidized to give at least one oxidation product (cyclic oxidation product) selected from a corresponding cycloalkyl hydroperoxide, cycloalkanol, and cycloalkanone. Typically, cyclopentane, if used as the raw material, gives cyclopentyl hydroperoxide and/or cyclopentanol and/or cyclopentanone; and cyclohexane, if used as the raw material, gives cyclohexyl hydroperoxide and/or cyclohexanol and/or cyclohexanone. Under some conditions, oxidative cleavage products such as glutaric acid and adipic acid may be produced as by-products. According to the method of the present invention, especially cycloalkanones can be obtained with a relatively high selectivity.

[Decomposition of Cycloalkyl Hydroperoxide]

After the oxidation of a cycloalkane, it is preferred to decompose and convert a cycloalkyl hydroperoxide contained in the oxidation product of the cycloalkane into a cycloalkanone and a cycloalkanol by mixing the cycloalkyl hydroperoxide with a basic aqueous solution having a pH of 12 or less in the presence of a nitrogen-containing cyclic compound containing a skeleton represented by Formula (I) as its ring constituent. This remarkably improves the production ratio of cycloalkanone to cycloalkanol in the oxidation product of the cycloalkane.

[Cycloalkyl Hydroperoxide]

Examples of the cycloalkyl hydroperoxide formed through oxidation of the cycloalkane include cycloalkyl hydroperoxides having 5 to 20 carbon atoms, of which cycloalkyl hydroperoxides having 5 to 10 carbon atoms are preferred.

Representative exemplary cycloalkyl hydroperoxides include cycloheptyl hydroperoxide, cyclohexyl hydroperoxide, cycloheptyl hydroperoxide, cyclooctyl hydroperoxide, cyclononyl hydroperoxide, cyclodecyl hydroperoxide, cyclododecyl hydroperoxide, cyclopentadecyl hydroperoxide, and cyclohexadecyl hydroperoxide. Each of different cycloalkyl hydroperoxides may be used alone or in combination.

A liquid containing a cycloalkyl hydroperoxide for use herein may be generally one having a concentration of cycloalkyl hydroperoxide of from about 0.1 to about 20 percent by weight. The cycloalkyl hydroperoxide-containing liquid may be a solution of the cycloalkyl hydroperoxide in an organic solvent (e.g., an aliphatic hydrocarbon, an alicyclic hydrocarbon, or an aromatic hydrocarbon) or may be a mixture that is obtained through oxidation of a corresponding cycloalkane (e.g., cyclopentane, cyclohexane, cycloheptane, cyclooctane, cyclononane, cyclodecane, cyclododecane, cyclopentadecane, or cyclohexadecane) typically with molecular oxygen and contains the cycloalkyl hydroperoxide. It should be noted that possible processes for oxidizing a cycloalkane include processes through liquid-phase catalytic oxidation, such as a process of oxidizing a cycloalkane using a transition metal compound such as a cobalt compound as a catalyst, but the present invention employs a method for oxidizing a cycloalkane using, as a catalyst, a nitrogen-containing cyclic compound containing a skeleton represented by Formula (I) as its ring constituent. In addition, the nitrogen-containing cyclic compound is also used as a catalyst in decomposition of a cycloalkyl hydroperoxide according to the present invention, whereby the reaction mixture obtained through oxidation of a cycloalkane in the presence of the nitrogen-containing cyclic compound can be used as the cycloalkyl hydroperoxide-containing liquid. When the reaction mixture is separated into an organic phase and an aqueous phase, the term "reaction mixture" as above refers to the organic phase; and this term includes a mixture obtained by subjecting the reaction mixture to a suitable treatment such as washing with water, extraction, separation into two liquids, dilution, and/or concentration.

Since a mixture being obtained through oxidation of a cycloalkane and containing a cycloalkyl hydroperoxide is used as the cycloalkyl hydroperoxide-containing liquid, the mixture generally further contains, in addition to the cycloalkyl hydroperoxide, unreacted cycloalkane and oxidation products such as a cycloalkanone, a cycloalkanol, a carboxylic acid, and an ester, but these components can be separated and recovered after subjecting the mixture to decomposition of the cycloalkyl hydroperoxide, and in this procedure, the cycloalkanone and cycloalkanol contained in the mixture can be separated and recovered together with a cycloalkanone and a cycloalkanol formed as a result of the decomposition of the cycloalkyl hydroperoxide.

[Catalyst]

The catalyst for use in decomposition of the cycloalkyl hydroperoxide can be the same catalyst as the one for use in the oxidation reaction of the cycloalkane (i.e., the nitrogen-containing cyclic compound). The production ratio of cycloalkanone to cycloalkanol can be significantly increased by using this compound and using a basic aqueous solution having a pH of 12 or less. Typically, the production ratio (by mole) is generally 2.0 or more and can be as high as 5.0 or more.

The amount of the nitrogen-containing cyclic compound is, for example, usually from 0.1 to 100 ppm by weight, preferably from 1 to 50 ppm by weight, and more preferably from 5 to 30 ppm by weight, relative to the amount of the cycloalkyl hydroperoxide-containing liquid. When a mixture being obtained though oxidation of a cycloalkane and containing a cycloalkyl hydroperoxide is used as the cycloalkyl hydroperoxide-containing liquid and when the nitrogen-containing cyclic compound is already contained in the mixture, it is preferred that the total amount of the nitrogen-containing cyclic compound already contained and of another portion of the nitrogen-containing cyclic compound newly added be within the above-specified range.

Additionally, a transition metal compound may be added to the system so as to accelerate the decomposition reaction of cycloalkyl hydroperoxide. Exemplary transition metal compounds include halides, organic acid salts, oxoacid salts, and complexes of transition metals including elements of Groups 3 to 12 of the Periodic Table of Elements, such as V, Mo, Mn, Fe, Ru, Co, and Cu. More specifically, by taking manganese compounds as an example, exemplary transition metal compounds include manganese chloride, manganese bromide, manganese acetate, manganese octoate, manganese naphthenate, manganese sulfate, manganese nitrate, and manganese acetylacetonate. Of transition metal compounds, manganese compounds and cobalt compounds are preferred, of which manganese compounds are more preferred. The amount of the transition metal compound in terms of metal is usually from 0.001 to 10 ppm by weight, preferably from 0.01 to 1 ppm by weight, and more preferably from 0.05 to 0.2 ppm by weight, relative to the amount of the cycloalkyl hydroperoxide-containing liquid.

[Basic Aqueous Solution having pH of 12 or Less]

The basic aqueous solution having a pH of 12 or less can be prepared by dissolving a basic substance in water. Preferred basic substances are alkali metal compounds other than alkali metal hydroxides; and alkaline earth metal compounds, and examples thereof include alkali metal carbonates such as sodium carbonate, potassium carbonate, sodium hydrogen carbonate, and potassium hydrogen carbonate; and alkaline earth metal carbonates such as calcium carbonate and magnesium carbonate. Each of different basic substances may be used alone or in combination.

The concentration of basic substances in the basic aqueous solution having a pH of 12 or less is usually from 1 to 50 percent by weight, preferably from 3 to 30 percent by weight, and more preferably from 5 to 25 percent by weight. It is enough for the pH of the basic aqueous solution to be 12 or less and more than 7, but is preferably from 7.5 to 12, more preferably from 8.5 to 12, and especially preferably from 9.5 to 12.

The proportion of the basic aqueous solution having a pH of 12 or less is usually from 0.1 to 30 percent by weight relative to the amount of the cycloalkyl hydroperoxide-containing liquid. When the cycloalkyl hydroperoxide-containing liquid contains acids and/or esters, it is desirable to mix the basic aqueous solution in an amount in terms of basic substance (alkali) of usually from 0.5 to 5 times by mole, preferably from 1 to 3 times by mole relative to the acids and esters, because the basic substance will be consumed by such acids and/or esters.

The temperature (reaction temperature) upon mixing of the cycloalkyl hydroperoxide-containing liquid with the basic aqueous solution having a pH of 12 or less to decompose the cycloalkyl hydroperoxide is usually from 20° C. to 200° C., and preferably from 50° C. to 160° C. The reaction pressure is usually from 0.1 to 5 MPa. The reaction may be carried out according to any system such as a batch system, semi-batch system, or continuous system.

As a result of the reaction, the cycloalkyl hydroperoxide is converted into a cycloalkanone and a cycloalkanol. According to the present invention, the reaction is carried out using the basic aqueous solution having a pH of 12 or less in the presence of the nitrogen-containing cyclic compound containing a skeleton represented by Formula (I) as its ring constituent. Accordingly, the production ratio of the cycloalkanone to the cycloalkanol is very high, and the cycloalkanone is prevented from oligomerization in a subsequent step, thus being very highly industrially useful.

After the completion of the reaction, a reaction product or products can be separated and purified according to a separation procedure such as filtration, concentration, distillation, extraction, crystallization, recrystallization, adsorption, or column chromatography, or any combination of them. More specifically, for example, the reaction mixture is separated into an oil phase and an aqueous phase, and the oil phase is distilled to give a cycloalkanone and a cycloalkanol. The resulting aqueous phase can be recycled and reused as a basic aqueous solution.

The resulting oxidation product of a cycloalkane produced by the method according to the present invention has a very high production ratio of a cycloalkanone and can be used as raw materials for polymers such as polyamides (nylons); and as intermediate materials for "fine chemicals".

In the above description, a method for producing an oxidation product of a cycloalkane through oxidation of the cycloalkane has been described. The same procedure (method) as above can be applied also to production of an aromatic carboxylic acid (such as benzoic acid or phthalic acid) through oxidation of an alkyl-substituted aromatic compound (such as toluene or xylene) or a lower-order oxide thereof (including an aromatic alcohol such as benzyl alcohol). Specifically, an aromatic carboxylic acid can be produced by oxidizing an alkyl-substituted aromatic compound or a lower-order oxide thereof in a liquid-liquid two phase system using an aqueous solvent in the presence of a nitrogen-containing cyclic compound containing a skeleton represented by Formula (I) as its ring constituent and having a solubility in water at 25° C. of 0.5 g/100 g-$H_2O$ or more. Also in this method, the reaction product can be easily separated from the catalyst after the completion of the reaction, and thereby the aromatic carboxylic acid can be industrially efficiently produced.

EXAMPLES

The present invention will be illustrated in further detail with reference to several examples below. It should be noted, however, these examples are never construed to limit the scope of the present invention.

(Product Analysis)

The amount of a cycloalkyl hydroperoxide was determined by adding triphenylphosphine as a reducing agent to a reaction mixture to convert the cycloalkyl hydroperoxide into a corresponding triphenylphosphine oxide and measuring the amount thereof through gas chromatography. The amounts of a cycloalkanol and a cycloalkanone were determined through gas chromatography. The actual amount of the produced cycloalkanol was determined by subtracting the amount of the cycloalkyl hydroperoxide from the amount of the cycloalkanol determined through gas chromatography.

(pH Measurement)

A pH was measured using a standard pH test paper supplied by TOYO ROSHI (measuring range: pH=1-14).

(Oxidation Reaction of Cycloalkane)

Example 1

In a 350-ml autoclave made of stainless steel SUS 316 and equipped with a stirrer were placed 80 g (1.14 mol) of cyclopentane and 2 g of a 5 percent by weight N-hydroxysuccinimide aqueous solution which contained 100 mg of N-hydroxysuccinimide dissolved therein, at room temperature (25° C.). The autoclave was hermetically sealed, pressurized to 3 MPa (gauge pressure) with a gaseous mixture of 50 percent by volume oxygen and 50 percent by volume nitrogen, and the aqueous solution therein was stirred at 150° C. for 1 hour. As a result, 39 mmol of cyclopentane reacted (with a conversion of 3.4%) and thereby yielded 9.4 mmol of cyclopentanone (with a selectivity of 24.1%), 4.8 mmol of cyclopentanol (with a selectivity of 12.3%), and 12.5 mmol of cyclopentyl hydroperoxide (with a selectivity of 32.1%). The total yield of cyclopentanone, cyclopentanol, and cyclopentyl hydroperoxide was 2.3%.

Example 2

In a 350-ml autoclave made of stainless steel SUS 316 and equipped with a stirrer were placed 80 g (0.95 mol) of cyclohexane and 2 g of a 5 percent by weight N-hydroxysuccinimide aqueous solution which contained 100 mg of N-hydroxysuccinimide dissolved therein, at room temperature (25° C.). The autoclave was hermetically sealed, pressurized to 3 MPa (gauge pressure) with a gaseous mixture of 50 percent by volume oxygen and 50 percent by volume nitrogen, and the aqueous solution therein was stirred at 150° C. for 1 hour. As a result, 36 mmol of cyclohexane reacted (with a conversion of 3.8%) and thereby yielded 9.2 mmol of cyclohexanone (with a selectivity of 25.6%), 4.6 mmol of cyclohexanol (with a selectivity of 12.8%), and 12.3 mmol of cyclohexyl hydroperoxide (with a selectivity of 34.2%). The total yield of cyclohexanone, cyclohexanol, and cyclohexyl hydroperoxide was 2.7%.

Comparative Example 1

In a 350-ml autoclave made of stainless steel SUS 316 and equipped with a stirrer were placed 80 g (1.14 mol) of cyclopentane and 100 mg of N-hydroxysuccinimide (these formed a slurry at room temperature (25° C.)). The autoclave was hermetically sealed, pressurized to 3 MPa (gauge pressure) with a gaseous mixture of 50 percent by volume oxygen and 50 percent by volume nitrogen, and the mixture therein was stirred at 150° C. for 1 hour. As a result, 8.8 mmol of cyclopentane reacted (with a conversion of 0.8%) and thereby yielded 0.5 mmol of cyclopentanone (with a selectivity of 5.7%), 0.2 mmol of cyclopentanol (with a selectivity of 2.3%), and 5.8 mmol of cyclopentyl hydroperoxide (with a selectivity of 65.9%). The total yield of cyclopentanone, cyclopentanol, and cyclopentyl hydroperoxide was 0.57%.

Comparative Example 2

In a 350-ml autoclave made of stainless steel SUS 316 and equipped with a stirrer were placed 80 g (1.14 mol) of cyclopentane, 100 mg of N-hydroxyphthalimide, and 1.9 g of water (these formed a slurry at room temperature (25° C.)). The autoclave was hermetically sealed, pressurized to 3 MPa (gauge pressure) with a gaseous mixture of 50 percent by volume oxygen and 50 percent by volume nitrogen, and the mixture therein was stirred at 150° C. for 1 hour. As a result, 8.2 mmol of cyclopentane reacted (with a conversion of 0.7%) and thereby yielded 0.5 mmol of cyclopentanone (with a selectivity of 6.1%), 0.2 mmol of cyclopentanol (with a selectivity of 2.4%), and 5.2 mmol of cyclopentyl hydroperoxide (with a selectivity of 63.4%). The total yield of cyclopentanone, cyclopentanol, and cyclopentyl hydroperoxide was 0.52%. N-hydroxyphthalimide has a solubility in water (25° C.) of 0.01 g/100 g-$H_2O$ or less.

Comparative Example 3

In a 350-ml autoclave made of stainless steel SUS 316 and equipped with a stirrer were placed 80 g (0.95 mol) of cyclohexane, 100 mg of N-hydroxyphthalimide, and 1.9 g of water (these formed a slurry at room temperature (25° C.)). The autoclave was hermetically sealed, pressurized to 3 MPa (gauge pressure) with a gaseous mixture of 50 percent by volume oxygen and 50 percent by volume nitrogen, and the mixture therein was stirred at 150° C. for 1 hour. As a result, 5.9 mmol of cyclohexane reacted (with a conversion of 0.7%) and thereby yielded 0.3 mmol of cyclohexanone (with a selectivity of 5.1%), 0.2 mmol of cyclohexanol (with a selectivity of 3.4%), and 3.8 mmol of cyclohexyl hydroperoxide (with a selectivity of 64.4%). The total yield of cyclohexanone, cyclohexanol, and cyclohexyl hydroperoxide was 0.45%. N-hydroxyphthalimide has a solubility in water (25° C.) of 0.01 g/100 g-$H_2O$ or less.

(Decomposition Reaction of Cyclopentyl Hydroperoxide)

Referential Example 1

A cyclopentyl hydroperoxide-containing liquid for use in the following examples and comparative examples was prepared by repeating the procedure of Example 1 two or more times, combining the resulting reaction mixtures, separating the total mixture into an organic phase and an aqueous phase, and recovering the organic phase. The recovered liquid contains, in terms of its composition, 97.3 percent by weight of cyclopentane, 0.88 percent by weight of cyclopentanone, 0.41 percent by weight of cyclopentanol, 1.20 percent by weight of cyclopentyl hydroperoxide, 0.21 percent by weight of esters (including 0.12 percent by weight of cyclopentyl esters in terms of cyclopentanol), and 13 ppm by weight of N-hydroxysuccinimide.

Example 3

In a 350-ml autoclave made of stainless steel SUS 316 and equipped with a stirrer were placed 70 g of the cyclopentyl hydroperoxide-containing liquid (with a cyclopentyl hydroperoxide concentration of 1.2 percent by weight) prepared in Referential Example 1, 10 g of a 20, percent by weight sodium carbonate aqueous solution (pH 11.5), and 0.035 mg of manganese acetate tetrahydrate (0.008 mg in terms of manganese (Mn)). The mixture in the autoclave was heated up to 130° C. in a nitrogen atmosphere at 3.5 MPa (gauge pressure) and then, stirred for 1 hour. The resulting reaction mixture was analyzed and found to contain 1.03 g of cyclopentanone, 0.35 g of cyclopentanol, 0.06 g of cyclopentyl hydroperoxide, and 0.02 g of esters (0.01 g of cyclopentyl esters in terms of cyclopentanol). The conversion from cyclopentyl hydroperoxide was 92.7%, the selectivity for cyclopentanone was 64.1% and the selectivity of cyclopentanol was 10.3% both on the basis of reacted cyclopentyl hydroperoxide. The production ratio (by mole) of cyclopentanone to cyclopentanol was 6.22.

Comparative Example 4

In a 350-ml autoclave made of stainless steel SUS 316 and equipped with a stirrer were placed 70 g of the cyclopentyl hydroperoxide-containing liquid (with a cyclopentyl hydroperoxide concentration of 1.2 percent by weight) prepared in Referential Example 1, 10 g of a 20 percent by weight sodium hydroxide aqueous solution (pH 14), and 0.035 mg of manganese acetate tetrahydrate (0.008 mg in terms of manganese). The mixture in the autoclave was heated up to 130° C. in a nitrogen atmosphere at 3.5 MPa (gauge pressure) and then, stirred for 1 hour. The resulting reaction mixture was analyzed and found to contain 0.63 g of cyclopentanone, 0.72 g of cyclopentanol, and 0.003 g of cyclopentyl hydroperoxide (and 0 g of esters). The conversion from cyclopentyl hydroperoxide was 99.7%, the selectivity for cyclopentanone was 2.3% and the selectivity for cyclopentanol was 60.6% both on the basis of reacted cyclopentyl hydroperoxide. The production ratio (by mole) of cyclopentanone to cyclopentanol was 0.038.

Example 4

In a 350-ml autoclave made of stainless steel SUS 316 and equipped with a stirrer were placed 70 g of the cyclopentyl hydroperoxide-containing liquid (with a cyclopentyl hydroperoxide concentration of 1.2 percent by weight) prepared in Referential Example 1 and 10 g of a 20 percent by weight sodium carbonate aqueous solution (pH 11.5). The mixture in the autoclave was heated up to 130° C. in a nitrogen atmosphere at 3.5 MPa (gauge pressure) and then, stirred for 1 hour. The resulting reaction mixture was analyzed and found to contain 0.99 g of cyclopentanone, 0.35 g of cyclopentanol, 0.18 g of cyclopentyl hydroperoxide, and 0.04 g of esters (0.02 g of cyclopentyl esters in terms of cyclopentanol). The conversion from cyclopentyl hydroperoxide was 78.8%, the selectivity for cyclopentanone was 68.9% and the selectivity for cyclopentanol was 11.2% both on the basis of reacted cyclopentyl hydroperoxide. The production ratio (by mole) of cyclopentanone to cyclopentanol was 6.15.

Comparative Example 5

In a 350-ml autoclave made of stainless steel SUS 316 and equipped with a stirrer were placed 70 g of the cyclopentyl hydroperoxide-containing liquid (with a cyclopentyl hydroperoxide concentration of 1.2 percent by weight) prepared in Referential Example 1 and 10 g of a 20 percent by weight sodium hydroxide aqueous solution (pH 14). The mixture in the autoclave was heated up to 130° C. in a nitrogen atmosphere at 3.5 MPa (gauge pressure) and then, stirred for 1 hour. The resulting reaction mixture was analyzed and found to contain 0.63 g of cyclopentanone, 0.69 g of cyclopentanol, and 0.13 g of cyclopentyl hydroperoxide (0 g of esters). The conversion from cyclopentyl hydroperoxide was 84.9%, the selectivity for cyclopentanone was 2.5% and the selectivity for cyclopentanol was 67.1% both on the basis of reacted cyclopentyl hydroperoxide. The production ratio (by mole) of cyclopentanone to cyclopentanol was 0.037.

The results are together shown in Tables 1 and 2. In these tables, the terms "peroxide", "anone", and "anol" refer to "cyclopentyl hydroperoxide, "cyclopentanone", and "cyclopentanol", respectively.

TABLE 1

| | | Oxidation reaction of cycloalkane | | | | |
|---|---|---|---|---|---|---|
| | Catalyst | Conversion from cycloalkane (%) | Selectivity for "anone" (%) | Selectivity for "anol" (%) | Selectivity for "peroxide" (%) | Total yield of "anone", "anol" and "peroxide" (%) |
| Example 1 | Aqueous solution of N-hydroxysuccinimide | 3.4 | 24.1 | 12.3 | 32.1 | 2.3 |
| Example 2 | Aqueous solution of N-hydroxysuccinimide | 3.8 | 25.6 | 12.8 | 34.2 | 2.7 |
| Com. Ex. 1 | Slurry of N-hydroxysuccinimide | 0.8 | 5.7 | 2.3 | 65.9 | 0.57 |
| Com. Ex. 2 | Slurry of N-hydroxyphthalimide | 0.7 | 6.1 | 2.4 | 63.4 | 0.52 |
| Com. Ex. 3 | Slurry of N-hydroxyphthalimide | 0.7 | 5.1 | 3.4 | 64.4 | 0.45 |

TABLE 2

| | Decomposition reaction of peroxide | | | | | | |
|---|---|---|---|---|---|---|---|
| | Peroxide content (g) | Base | Metal | Conversion from peroxide (%) | Selectivity for "anone" (%) | Selectivity for "anol" (%) | Ratio (by mole) of "anone" to "anol" |
| Example 3 | 70 | 10 g of 20% Na$_2$CO$_3$ | 0.008 mg of Mn | 92.7 | 64.1 | 10.3 | 6.22 |
| Example 4 | 70 | 10 g of 20% Na$_2$CO$_3$ | — | 78.8 | 68.9 | 11.2 | 6.15 |
| Com. Ex. 4 | 70 | 10 g of 20% NaOH | 0.008 mg of Mn | 99.7 | 2.3 | 60.6 | 0.038 |
| Com. Ex. 5 | 70 | 10 g of 20% NaOH | — | 84.9 | 2.5 | 67.1 | 0.037 |

INDUSTRIAL APPLICABILITY

According to the present invention, there is provided a method for industrially efficiently producing, from a cycloalkane, a corresponding useful oxidation product such as a cycloalkyl hydroperoxide, a cycloalkanol, and/or a cycloalkanone, above all an especially useful cycloalkanone, with a high selectivity in a good yield at low cost. The method is advantageous in respect of energy and process. The resulting oxidation products obtained by the method according to the present invention are useful typically as raw materials for the production of polymeric compounds such as polyamide polymeric compounds; and as intermediate materials for "fine chemicals".

The invention claimed is:

1. A method for producing an oxidation product of a cycloalkane, the method comprising the step of oxidizing the cycloalkane in a liquid-liquid two phase system using an aqueous solvent in the presence of a nitrogen-containing cyclic compound to give an oxidation product of the cycloalkane, the nitrogen-containing cyclic compound containing, as its ring constituent, a skeleton represented by the following Formula (I):

[Chemical Formula 1]

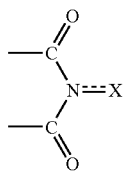
(I)

wherein X represents an oxygen atom or an —OR group, and wherein R represents a hydrogen atom or a hydroxyl-protecting group, the nitrogen-containing cyclic compound having a solubility in water at 25° C. of 0.5 g/100 g-$H_2O$ or more.

2. A method for producing an oxidation product of a cycloalkane, according to claim 1, wherein N-hydroxysuccinimide is used as the nitrogen-containing cyclic compound.

3. A method for producing an oxidation product of a cycloalkane, according to claim 1 or 2, further comprising, subsequent to the step of oxidizing the cycloalkane, the step of mixing a cycloalkyl hydroperoxide contained in the oxidation product of the cycloalkane with a basic aqueous solution having a pH of 12 or less in the presence of a nitrogen-containing cyclic compound containing the skeleton of Formula (I) as its ring constituent, to decompose and convert the cycloalkyl hydroperoxide into a cycloalkanone and a cycloalkanol.

4. A method for producing an oxidation product of a cycloalkane, according to claim 3, wherein the basic aqueous solution is an aqueous solution containing a compound selected from the group consisting of alkali metal carbonates and alkaline earth metal carbonates.

5. A method for producing an oxidation product of a cycloalkane, according to claim 1 or 2, wherein the concentration of the nitrogen-containing cyclic compound in a reaction system is from 0.02 to 0.6 percent by weight based on the total amount of a reaction mixture.

* * * * *